(12) United States Patent
Drinkwater et al.

(10) Patent No.: US 7,101,849 B1
(45) Date of Patent: Sep. 5, 2006

(54) ωCONOTOXIN PEPTIDES

(75) Inventors: Roger Desmond Drinkwater, Kenmore (AU); Richard James Lewis, Woolloogabba (AU); Paul Francis Alewood, Moggill (AU); Katherine Justine Nielsen, Chapel Hill (AU)

(73) Assignee: The University of Queensland, Queensland (AU)

( * ) Notice: Subject to any disclaimer, the term of this patent is extended or adjusted under 35 U.S.C. 154(b) by 0 days.

(21) Appl. No.: 09/673,490

(22) PCT Filed: Apr. 16, 1999

(86) PCT No.: PCT/AU99/00288
§ 371 (c)(1),
(2), (4) Date: Dec. 11, 2000

(87) PCT Pub. No.: WO99/54350
PCT Pub. Date: Oct. 28, 1999

(30) Foreign Application Priority Data
Apr. 16, 1998 (AU) .............................................. PP2989
Feb. 1, 1999 (AU) .............................................. PP8419

(51) Int. Cl.
*A61K 38/17* (2006.01)
*C07K 14/435* (2006.01)
*G01N 33/53* (2006.01)

(52) U.S. Cl. ............................ 514/12; 514/2; 530/325; 530/300; 435/7.2

(58) Field of Classification Search ..................... 514/2, 514/12; 530/325, 300; 435/7.2
See application file for complete search history.

(56) References Cited

U.S. PATENT DOCUMENTS 5,364,842 A * 11/1994 Justice et al. .................. 514/12
5,424,218 A * 6/1995 Miljanich et al. ........... 436/503

OTHER PUBLICATIONS

K.J. Nielsen et al., (1996) "A Consensus Structure for ω–Conotoxins with Different Selectivities for Voltage–sensitive Calcium Channel Subtypes: Comparison of MVIIA, SVIB and SNX–202", (Journal of Molecular Biology, vol. 263, pp. 297–310.

K. Sato et al. (1997), "Binding of Chimeric Analogs of ω–Conotoxin MVIIA and MVIIC to the N–and P70–type Calcium Channels", (FEBS Letters, vol. 414, pp., 480–484.

* cited by examiner

*Primary Examiner*—Gabriele Bugaisky
(74) *Attorney, Agent, or Firm*—Scully, Scott, Murphy & Presser

(57) ABSTRACT

An isolated, synthetic, or recombinant ω-conotoxin peptide in which the fourth loop between cysteine residues 5 and 6 comprises SEQ ID NO: 1 or such a sequence which has undergone one or more amino acid substitutions or side chain modifications, and uses therefor. SEQ ID NO: 1 comprises the amino acid sequence SGTVGR.

13 Claims, 1 Drawing Sheet

FIGURE 1 atcatcaaa

| 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|
| ATG | AAA | CTG | ACG | TGT | GTG | GTG | ATC | GTC | GCC | GTG | CTG | CTC | CTG | ACG |
| M | K | L | T | C | V | V | I | V | A | V | L | L | L | T |

| 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|
| GCC | TGT | CAA | CTC | ATC | ACA | GCT | AAT | GAC | TCC | AGA | GGT | ACG | CAG | AAG |
| A | C | Q | L | I | T | A | N | D | S | R | G | T | Q | K |

| 31 | 32 | 33 | 34 | 35 | 36 | 37 | 38 | 39 | 40 | 41 | 42 | 43 | 44 | 45 |
|---|---|---|---|---|---|---|---|---|---|---|---|---|---|---|
| CAT | CGT | GCC | CTG | AGG | TCG | GAC | ACC | AAA | CTC | TCC | ATG | TCG | ACT | CGC |
| H | R | A | L | R | S | D | T | K | L | S | M | S | T | R |

| 46 | 47 | 48 | 49 | 50 | 51 | 52 | 53 | 54 | 55 | 56 | 57 | 58 | 59 | 60 |
|---|---|---|---|---|---|---|---|---|---|---|---|---|---|---|
| TGC | AAG | AGT | AAA | GGA | GCA | AAA | TGT | TCA | AAG | CTT | ATG | TAT | GAC | TGC |
| C | K | S | K | G | A | K | C | S | K | L | M | Y | D | C |

| 61 | 62 | 63 | 64 | 65 | 66 | 67 | 68 | 69 | 70 | 71 | 72 | 73 | 74 |
|---|---|---|---|---|---|---|---|---|---|---|---|---|---|
| TGC | AGC | GGT | TCT | TGC | AGC | GGC | ACC | GTA | GGT | AGA | TGT | GGC | TGA |
| C | S | G | S | C | S | G | T | V | G | R | C | G | * | ggcgcttgatctcccccttctgtgctcatctttctgccgagtcctcttacctgagagtggtgtcatgaaccactcatcactacccctgaggt
ctcaaagaactactgaaataaagccgcttgaaaaaaaaaaa tcc

ωCONOTOXIN PEPTIDES

This invention relates to novel peptides of the omega conotoxin (ω-conotoxin) class, and their use as pharmacological tools and in any indication where blockade of N-type calcium channels may be of benefit, for example in the reduction of neuronal damage following ischemia, production of analgesia, or enhancement of opiate analgesia, in the treatment of schizophrenia, stimulant induced psychoses, hypertension, inflammation and diseases which cause bronchoconstriction, and in the inhibition of progression of neuropathic pain. The invention also relates to pharmaceutical compositions comprising these peptides and to nucleic acid probes useful in finding useful analogues of these peptides.

Predatory marine snails of the genus *Conus* (cone snails) are a diverse family of marine molluscs that immobilise their prey through the injection of venom. The venom is a complex mixture of peptides, known as conotoxins, which target a variety of different kinds of cellular receptor. The mixture of peptides that are found in the venom varies amongst species of cone snails as does the prey upon which the molluscs feed.

One particular family of peptides, known as the ω-conotoxins, isolated from such venoms have been found to target and block voltage sensitive calcium channels (VSCCs). These ω-conotoxins are reasonably small peptides (typically 24 to 32 amino acids) with six characteristic cysteine substitutions and a pattern of disulfide bonds. The pattern of the disulfide links and the distribution of the cysteine residues mean that the peptide nay notionally be considered to comprise four loops. The amino acids between cysteine residues 1 and 2, 2 and 3, 4 and 5, and 5 and 6 define loops, while cysteine residues 3 and 4 are adjacent.

Studies of different w-conotoxins which have been either isolated from the complex peptide venoms of a variety of different species of *Conus*, or synthesised as chemical variants of known w-conotoxins has provided an array of ω-conotoxins which display varying affinity and selectivity for various subtypes of neuronal calcium channels. Such is the affinity of some of these peptides for VSCCs that a number of the ω-conotoxins have become important research tools for defining different subtypes of neuronal voltage sensitive calcium channel.

In mammalian systems, ω-conotoxins such as GVIA have a high level of selectivity for N-type calcium channels whilst other ω-conotoxins such as MVIIC have a low affinity for the N-type channel but bind strongly to P/Q-type channels. Labelled forms of these ligands (for example $^{125}$Iodinated MVIIA) are routinely used in pharmacological assays relating to VSCCs.

Whilst the available conotoxins are useful in defining a number of calcium channel sub-types new ligands displaying different binding profiles and affinities may be useful in further defining channel sub-types.

In addition to their use as research tools, conotoxins which target N-type calcium channels have been proposed for use in the treatment of a variety of conditions including ischaemia induced brain injury, acute psychotic episodes which may be drug induced or result from a psychiatric disorder, diseases which cause bronchoconstriction, hypertension, inflammation and chronic pain. They may also be used in the treatment of schizophrenia, in the production of analgesia and the enhancement of opiate induced analgesia. The compounds of the invention may be useful in any indication where blockade of N-type calcium channels may be of benefit. One particular conotoxin, known as MVIIA or, in its synthetic form, SNX-111, is in clinical trials for some of these applications.

Despite these advances in the use of ω-conotoxins the presently available compounds are not ideal therapeutics. For example, SNX-111 has been reported to cause hypotension as a result of action at peripheral channels. Another of the conotoxins, GVIA, is a potent antagonist of N-type calcium channels but binds to such channels in an irreversible manner, and accordingly is unsuitable as a therapeutic. Many other of the known ω-conotoxins do not have an adequate level of selectivity for the N-type channel to be deemed suitable therapeutic candidates; blockade of P/Q-type channels may lead to death.

Accordingly there exists a need for new therapeutic agents which have a selectivity for N-type calcium channels over P/Q type channels, and which may be useful in the treatment of conditions related to N-type calcium channels.

In a first aspect of the present invention there is provided an isolated, synthetic or recombinant ω-conotoxin peptide in which the fourth loop between cysteine residues 5 and 6 comprises the following sequence of amino acids:

SGTVGR [SEQ ID NO: 1]

or such a sequence which has undergone one or more amino acid substitutions, or side chain modifications.

Preferably the fourth loop consists of the above sequence, or such a sequence which has undergone one or more conservative amino acid substitutions or side chain modifications.

Preferably each of the first, second and third loops of the conotoxin peptide correspond to the loop of a naturally occurring ω-conotoxin peptide, or such a sequence of amino acids which has undergone one or more amino acid substitutions, additions or deletions.

Substitutions encompass amino acid alterations in which an amino acid is replaced with a different naturally-occurring or a non-conventional amino acid residue. Such substitutions may be classified as "conservative", in which case an amino acid residue contained in a polypeptide is replaced with another naturally-occurring amino acid of similar character, for example Gly-Ala, Val-Ile-Leu, Asp-Glu, Lys-Arg, Asn-Gln or Phe-Trp-Tyr. It is to be understood that some non-conventional amino acids may also be suitable replacements for the naturally occurring amino acids. For example ornithine, homoarginine and dimethyllycine are related to His, Arg and Lys.

Substitutions encompassed by the present invention may also be "non-conservative", in which an amino acid residue which is present in a polypeptide is substituted with an amino acid having different properties, such as naturally-occuring amino acid from a different group (eg. substituting a charged or hydrophobic amino acid with alanine), or alternatively, in which a naturally-occurring amino acid is substituted with a non-conventional amino acid.

Amino acid substitutions are typically of single residues, but may be of multiple residues, either clustered or dispersed.

Preferably, amino acid substitutions are conservative.

Additions encompass the addition of one or more naturally occurring or non-conventional amino acid residues. Deletion encompasses the deletion of one or more amino acid residues.

As stated above the present invention includes peptides in which one or more of the amino acids has undergone sidechain modifications. Examples of side chain modifications contemplated by the present invention include modifications of amino groups such as by reductive alkylation by a reaction with an aldehyde followed by reduction with NaBH$_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH. Any modification of cysteine residues must not affect the ability of the peptide to form the necessary disulphide bonds. It is also possible to replace the sulphydryl group of cysteine with selenium equivalents such that the peptide forms a diselenium bond in place of one or more of the disulphide bonds.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Proline residue may be modified by, for example, hydroxylation in the 4-position.

Some amino acid residues, for example methionine, may under some conditions be prone to oxidation. In some cases the oxidised residue may retain biological activity similar to that of the parent peptide and accordingly the oxidised form of the peptides are considered within the scope of the present invention, for example CVID where the methionine residue is oxidised. However, oxidation of an amino acid residue may in some cases lead to a decrease in activity or selectivity. Accordingly, where oxidisable residues are present they may be replaced with another amino acid. Replacement may be with an amino acid having similar properties, for example charge and size, or may be with an amino acid having different properties. For example, in the case of CVID the methionine residue at position 12 may be replaced with, for example, norleucine, O-methyl serine, O-methyl homoserine or alanine.

A list of some amino acids having modified side chains and other unnatural amino acids are shown in Table 1.

TABLE 1

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
| | | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
| | | L-N-methylglutamic acid | Nmglu |
| cyclohexylalanine | | Chexa L-N-methylhistidine | Nmhis |
| cyclopentylalanine | Cpen | L-N-methylisoleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |

TABLE 1-continued

| Non-conventional amino acid | Code | Non-conventional amino acid | Code |
|---|---|---|---|
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl-ethylamino)cyclopropane | Nmbc | L-O-methyl serine | Ornser |
| | | L-O-methyl homoserine | Ornhser |

These types of modifications may be important to stabilise the peptide if administered to an individual or for use as a diagnostic reagent. Other modifications may be made to the peptide in order to stabilise it or enhance other of its properties, for example membrane penetration or solubility. Such modifications include modifying the side chain of one or more amino acids to attach other types of group, for example a lipophilic group. Such attachment may be made through a liking group designed to space the other group or groups away from the peptide so as not to interfere with the activity of the peptide. Those skilled in the art will readily be able to determine how to modify the peptides of the invention. All such modified forms of the peptide are considered within the scope of the present invention.

Other derivatives contemplated by the present invention include a range of glycosylation variants from a completely unglycosylated molecule to a modified glycosylated molecule. Altered glycosylation patterns may result from expression of recombinant molecules in different host cells.

The ω-conotoxins of the present invention are typically amidated at the C-terminal however compounds with a free carboxyl terminus or other modifications at the C-terminal are considered to be within the scope of the present invention. Preferably the peptides are amidated or have a free carboxyl.

Preferably the peptides will retain the Cys residues and characteristic disulphide bonding pattern. Peptides may include additional Cys residues provided they are protected during formation of the disulphide bonds.

Preferably the peptide has a second loop which comprises a sequence selected from:

| | |
|---|---|
| SKLMYD | [SEQ ID NO: 2], |
| SRLMYD | [SEQ ID NO: 3], |
| DRLMYD | [SEQ ID NO: 4], |
| DKLMYD | [SEQ ID NO: 33], |
| SKLAYD | [SEQ ID NO: 34], |
| SKLNleYD | [SEQ ID NO: 35], |
| SRLNleYD | [SEQ ID NO: 36], |
| SKLOhrnhserYD | [SEQ ID NO: 37], |
| SKLOrnserYD | [SEQ ID NO: 38], | or such a sequence which has undergone one or more conservative amino acid substitution or side chain modifications.

In a particularly preferred embodiment the conotoxin peptide has the following sequence:

CVID (1)  C<u>KSKGAK</u>C<u>SKLMYD</u>CC<u>SGSC</u>S<u>GTVGRC</u> [SEQ ID NO:5]
              1        2        3       4

The four loops are shown underlined. This peptide was isolated from *Conus catus* and has been designated herein as CVID. The peptide has been shown to have a high potency and a high selectivity for N-type calcium channel over P/Q-type calcium channel in receptor binding assays. Two modified forms of CVID have also been shown to have a high potency and high selectivity for N-type calcium channel. These are designated $R^{10}$-CVID and $D^9R^{10}$-CVID as follows:

$R^{10}$-CVID (2) CKSKGAKCSRLMYDCCSGSCS-GTVGRC [SEQ ID NO: 6]
$D^9R^{10}$-CVID (3) CKSKGAKCDRLMYDCCSGSCS-GTVGRC [SEQ ID NO: 71]

The peptides according to the present invention may be naturally occurring conotoxin peptides, such as CVID, or may be derivatives of such naturally occurring peptides. The derivatives of the naturally occurring conotoxin peptides may differ from their naturally occurring counterparts by one or more amino acid substitutions, deletions or additions as described above.

In modification to form derivatives of naturally occurring peptides it is useful to compare the amino acid sequences of active naturally occurring peptides to determine which, if any, of the residues are conserved between active species. Substitution of these conserved residues, while not prohibited, is less favoured than substitutions of on-conserved residues.

Derivatives where Ala replaces one or more residues can be used to identify the pharmacophore. Preferably only one or two amino acids is replaced with Ala at a time. Additional new peptides can be made where charged, polar or hydrophobic residues, respectively, are replaced to assist defining more precisely the type of interactions involved in the binding of this pharmacological class of peptide to its receptor. Non-conservative replacements, where charge is reversed, or polar residues replace hydrophobic residues, can further identify residues involved in binding. All of these peptides have potential to show improved potency, or greater selectivity. Non-native amino acid changes could also be included to improve potency, selectivity and/or stability.

Exposed residues are most likely to be involved in receptor binding and can be systematically replaced. Particular emphasis is placed on changing residues involved in binding and residues just on the periphery of the pharmacophore, using longer side chain forms or non-conserved changes to pick up additional binding interactions for improved potency and/or selectivity.

Three-dimensional $^1$H NMR studies, of the type known to those skilled in the art (Nielsen et al. 1996 and 1999) and further described in Example 5, indicate that CVID adopts a similar fold to known ω-conotoxins such as MVIIA. However, unlike those ω-conotoxins, loop 4 of CVID is found in a different orientation to that of the known ω-conotoxins and CVID also has two hydrogen bonds which hold loops 2 and 4 together; factors that may contribute to the ability of CVID to discriminate among VSCCs.

In view of this novel confirmation of loop 4 and the stabilisation between loops 2 and 4 of CVID, one preferred group of derivatives are those which maintain an orientation of loop 4 similar to that seen in CVID. A further preferred group of derivatives are those ω-conotoxins which have an interaction or interactions between loops 2 and 4 which stabilise the confirmation of loops 2 and 4. Those skilled in the art may readily determine the three-dimensional structure of particular peptides, the orientation of loop 4 and interactions between the loops.

Another preferred group of derivatives are those which maintain or only have conservative substitutions at residues 10, 11, 22 and 23 of CVID.

In another embodiment of the present invention there is provided a chimeric ω-conotoxin peptide in which one or more of loops 1 to 3 of conotoxin CVID have been substituted with the corresponding loop of a different co-conotoxin.

A preferred group of derivatives of CVID are those ω-conotoxin peptides which maintain certain residues of CVID. These derivatives are represented in the following sequence CxxxGxxCxKLxYxCCxSCSGxVGRC [SEQ ID NO: 39]

where each x may be any other amino acid and up to one x may be a deletion Preferred selections for x would be the corresponding natural amino acids from ω-conopeptides with N-type BSCC selectivity and conservative substitutions or alanine substitutions of those amino acids, all of which may also have modified side chains. For example, methionine may be replaced with O-methyl serine or O-methyl homoserine.

Some known conotoxins are as follows:

| | |
|---|---|
| MVIIA (SNX-III) | CKGKGAKCSRLMYDCCTGSCRSGKC [SEQ ID NO: 8] |
| MVIIC | CKGKOAPCRKTMYDCCSGSCGRRGKC [SEQ ID NO: 9] |
| GVIA | CKSOGSSCSOTSYNCCRSCNOYTKRCY [SEQ ID NO: 10] |

In the sequence for GVIA the "O" refers to 4-hydroxy proline (Hyp). This amino acid residue results from post transitional modification of the encoded peptide and is not directly encoded by the nucleotide sequence.

Chimeric ω-conotoxins contemplated by the present invention include DADD, DAGD and GGGD. Where a D, A or a 0 represent loops selected from CVID, MVIIA or GVIA respectively. Accordingly DADD corresponds to loops 1, 3 and 4 being selected from. CVID and loop 2 being selected from MvIIA, tis chimeric c-conotoxin is the same as $R^{10}$-CVID.

A number of other ω-conotoxin peptides according to the invention were found to be encoded by mRNA isolated from *Conus catus* according to the general procedure described in Example 3. These encoded peptides were synthesised by standard procedures and may be considered as derivatives of CVID, the sequences are as follows:

| | |
|---|---|
| (4) CRSKGAKCSKLMYDCCSGSCSGTVGRC | [SEQ ID NO: 14] |
| (5) CKSKGARCSKLMYDCCSGSCSGTVGRC | [SEQ ID NO: 15] |
| (6) CKSKGAQCSKLMYDCCSGSCSGTVGRC | [SEQ ID NO: 16] |
| (7) CKSKGAKCSKLMYDCCSGSCSGAVGRC | [SEQ ID NO: 17] |

Examples of other derivatives of CVID include the following sequences:

| | | |
|---|---|---|
| (8) | CKSKGAKCDKLMYDCCSGSCSGTVGRC | [SEQ ID NO: 18] |
| (9) | CKYKGAKCSRLMYDCCSGSCSGTVGRC | [SEQ ID NO: 19] |
| (10) | CKSKGAKCSKLAYDCCSGSCSGTVGRC | [SEQ ID NO: 20] |
| (11) | CKSKGAKCSKLMYDCCTGSCSGTVGRC | [SEQ ID NO: 21] |
| (12) | CKSKDalAKCSKLMYDCCSGSCSGTVGRC | [SEQ ID NO: 22] |
| (13) | CKSKGAKCSKLMYDCCSGSCSGTVGRCY | [SEQ ID NO: 23] |
| (14) | CKSKGAKCSKLMYDCCSGSCSGTVGRC | [SEQ ID NO: 24] |
| (15) | YCKSKGAKCSKLMYDCCSGSCSGTVGRC | [SEQ ID NO: 25] |
| (16) | CKSKGAKCSKLMYDCCSGSCSGTVGRC | [SEQ ID NO: 26] |
| (17) | CKSKGAKCSKLNleYDCCSGSCSGTVGRC | [SEQ ID NO: 27] |
| (18) | CKSKGAKCSRLNleYDCCSGSCSGTVGRC | [SEQ ID NO: 28] |
| (19) | CKYKGAKCSRLNleYDCCSGSCSGTVGRC | [SEQ ID NO: 29] |
| (20) | CKSKGAKCSKLOrnhserYDCCSGSCSGTVGRC | [SEQ ID NO: 30] |
| (21) | CKSXGAKCSKLOrnserYDCCSGSCSGTVGRC | [SEQ ID NO: 31] |
| (22) | CKSKGAKCSKLM(O)YDCCSGSCSGTVGRC | [SEQ ID NO: 32] |

Compounds (13) and (15) (SEQ ID NOS: 23 and 25) have an additional amino acid at the C-terminal and N-terminal respectively.

Compound (14) (SEQ ID NO: 24) has a free carboxyl at the C-terminal.

Compound (16) (SEQ ID NO: 26) is acylated at the N-terminal.

Compound (22) (SEQ ID NO: 32) has the methionine residue at position 12 oxidised to its sulfoxide, as indicated by (O).

Compounds (10), (17), (18), (19), (20) and (21) (SEQ ID NOS: 20, 27, 25, 29, 30 and 31, respectively) represent methionine replacements at position 12.

A preferred group of ω-conotoxin peptides are CVID, compounds (4), (5), (10), (17), (18), (20), and (21). A particularly preferred-conotoxin peptides is CVID.

In the accompanying sequence listing the amino acids Xaa are as shown in Table 2.

TABLE 2

| SEQ ID NO: | Xaa |
|---|---|
| SEQ ID NO: 22 | Dal |
| SEQ ID NO: 27 | Nle |
| SEQ ID NO: 28 | Nle |
| SEQ ID NO: 29 | Nle |
| SEQ ID NO: 30 | Ornhser |
| SEQ ID NO: 31 | Ornser |
| SEQ ID NO: 35 | Nle |
| SEQ ID NO: 36 | Nle |
| SEQ ID NO: 37 | Ornhser |
| SEQ ID NO: 38 | Ornser |

The peptides according to the present invention preferably have a selectivity for N-type calcium channel over P/Q type calcium channel. The terms "selective" and "selectivity" as used herein mean that the binding activity of the peptide at the N-type calcium channel is greater than the binding activity at the P/Q-type calcium channel. Those skilled in the art would be able to readily determine the selectivity of the peptides for these calcium channels using standard techniques.

Iodinated GVIA and MVIIC are high affinity ligands for the N-type and P/Q type calcium channel receptors respectively and are routinely used in receptor binding assays (Kristipati et al., 1994; Nadasdi et at., 1995). Such assays may be used to test the calcium channel binding activity of the peptides of the present invention. Functional assays such as those described by Lew et al. (1997) may also be useful in determining activity at N-type calcium channels. The peptides according to the present invention may also be used in such assays.

The ω-conotoxins of the present invention may be used, typically in labelled form such as radioiodinated CVID, to run assays and/or screens to identify compounds which interact with N-type calcium channels and/or particular subtypes of such channels. Those skilled in the art could readily establish such assays and/or screens. A variety of labelled versions of the compounds of the present invention may be readily prepared by standard methods and assessed for retention of their ability to bind to N-type calcium channels in standard assays. Labelled versions of the compounds which do retain the ability to bind to N-type calcium channels or binding portions of such channels could then be used in assays and/or screens. Accordingly, the present invention extends to the use of the peptides of the invention in screens to identify compounds with activity at N-type VSCCs.

The conotoxins of the present invention may be prepared using standard peptide synthetic methods followed by oxidative disulfide bond formation. For example, the linear peptides may be synthesised by solid phase methodology using BOC chemistry, as described by Schnoltzer et al (1992). Following deprotection and cleavage from the solid support the reduced peptides are purified using preparative chromatography. The purified reduced peptides are oxidised in buffered systems, for example as described in example 2. The oxidised peptides were purified using preparative chromatography.

References describing the synthesis of conotoxins include Sato et al, Lew et al and WO 91/07980.

The conotoxins may also be prepared using recombinant DNA technology. A nucleotide sequence encoding the desired peptide sequence may be inserted into a suitable vector and protein expressed in an appropriate expression system. In some instances, further chemical modification of the expressed peptide may be appropriate, for example C-terminal amidation. Under some circumstances it may be desirable to undertake oxidative bond formation of the expressed peptide as a chemical step following peptide expression. This may be preceded by a reductive step to provide the unfolded peptide. Those skilled in the art may readily determine appropriate conditions for the reduction and oxidation of the peptide.

Naturally occurring CVID was isolated from Conus catus by assay guided fractionation of the venom followed by sequencing of the purified peptide.

The invention further provides an isolated nucleic acid molecule comprising a sequence of nucleotides encoding or complementary to sequence encoding a conotoxin peptide as described above.

In a further aspect of the present invention there is provided a nucleic acid probe comprising a sequence of nucleotides encoding or complementary to a sequence encoding ω-conotoxin peptides having a fourth loop of CVID, said probe encoding or complementary to all or part of loop 4 of the ω-conotoxin CVID, or such a sequence which has undergone one or more amino acid substitution or side chain modifications.

In a particularly preferred embodiment the nucleic acid probe comprises a sequence of nucleotides encoding or complementary to a sequence encoding the sequence shown in SEQ ID NO: 1.

As used herein a reference to a "probe" includes reference to a primer used in amplification or a probe for use in direct hybridization.

Still another aspect of the present invention is directed to antibodies to the ω-conotoxin peptides according to the invention. Such antibodies may be monoclonal or polyclonal and may be selected from naturally occurring antibodies to the peptides or may be specifically raised to the peptides using standard techniques. In the case of the latter, the peptides may first need to be associated with a carrier molecule. The antibodies of the present invention are particularly useful as therapeutic or diagnostic agents.

In this regard, specific antibodies can be used to screen for the peptides according to the invention. Techniques for such assays are well known in the art and include, for example, sandwich assays and ELISA Knowledge of peptide levels may be important for monitoring certain therapeutic protocols.

The nucleic acid molecules of the present invention may be DNA or RNA When the nucleic acid molecule is in DNA form, it may be genomic DNA or cDNA RNA forms of the nucleic acid molecules of the present invention are generally mRNA.

Although the nucleic acid molecules of the present invention are generally in isolated form, they may be integrated into or ligated to or otherwise fused or associated with other genetic molecules such as vector molecules and in particular expression vector molecules. Vectors and expression vectors are generally capable of replication and, if applicable, expression in one or both of a prokaryotic cell or a eukaryotic cell. Preferably, prokaryotic cells include *E. coli*, *Bacillus* sp and *Pseudomonas* sp. Preferred eukaryotic cells include yeast, fungal, mammalian and insect cells.

Accordingly, another aspect of the present invention contemplates a genetic construct comprising a vector portion and a gene capable of encoding a peptide according to the invention.

Preferably, the gene portion of the genetic construct is operably linked to a promoter on the vector such that said promoter is capable of directing expression of the gene portion in an appropriate cell.

The present invention extends to such genetic constructs and to prokaryotic or eukaryotic cells comprising same.

In view of their high potency and selectivity towards N-type calcium channel over P/Q type the ω-conotoxin peptides of the present invention may be useful in any indications where blockade of N-type calcium channels may be of benefit. Such indications include the reduction of neuronal damage following ischemia, production of analgesia, enhancement of opiate analgesia, treatment of schizophrenia, stimulant psychoses, hypertension, inflammation and diseases which cause bronchoconstriction, and inhibition of progression of neuropathic pain. Analgesia means the relief of pain generally and includes relief of acute, persistent or neuropathic pain. Preferred indications where the peptides may be useful include production of analgesia, enhancement of opiate analgesia, and inhibition of progression of neuropathic pain.

Assays useful for assessing compounds with activity at N-type calcium channels, such as the ω-conotoxins of the present invention, may be in vitro or in vivo assays and are known to those skilled in the art. Examples of assays include those described or referenced in WO91/07980, WO93/13128, U.S. Pat. No. 5,824,645, WO97/04797, Drugs of the Future (1994 and 1998), Drug Data Report (1993), or Heading (1999).

Particular assays which may be of use include; in vitro binding assays; nociceptive tests such as the formalin test and the hot-plate tests (Molmberg and Yaksh, 1995), the tail flick and mechanical paw pressure tests (Omote et al., 1996), or models of neuropathic pain (White and Cousins, 1998); neuroprotective tests such as the rat 4-vessel occlusion model or in vitro cell survival assays; other assays looking at effects on neurotransmitter release, for example Substance P (Ray et al., 1991; Cabot et al., 1998).

The ω-conotoxins of the present invention have shown useful activity in some of these assays.

Accordingly in a further aspect of the present invention there is provided a composition comprising: an isolated, synthetic or recombinant-conotoxin peptide in which the fourth loop between cysteine residues 5 and 6 comprises the following sequence of amino acids:

SGTVGR [SEQ ID NO: 1]

or such a sequence which has undergone one or more conservative amino acid substitutions, and a pharmaceutically acceptable carrier or diluent.

Preferably the composition is in the form of a pharmaceutical composition.

There is also provided the use of an isolated, synthetic or recombinant ω-conotoxin peptide in which the fourth loop between cysteine residues 5 and 6 comprises the following sequence of amino acids:

SGTVGR [SEQ ID NO: 1]

or such a sequence which has undergone one or more conservative amino acid substitutions or side chain modifications in the manufacture of a medicament for the reduction of neuronal damage following ischemia, production of analgesia, enhancement of opiate analgesia, treatment of schizophrenia or the treatment of stimulant psychoses, hypertension, inflammation, diseases which cause bronchoconstriction, or for inhibition of progression of neuropathic pain.

The invention further provides a method for reducing neuronal damage following ischemia, for the production of analgesia, for enhancement of opiate analgesia, for the treatment of schizophrenia, stimulant psychoses, hypertension, inflammation, diseases which cause bronchoconstriction, or for inhibition of progression of neuropathic pain, including the step of administering to a mammal an effective amount of an isolated or recombinant ω-conotoxin peptide in which the fourth loop between cysteine residues 5 and 6 comprises the following sequence of amino acids:

SGTVGR [SEQ ID NO: 1]

or such a sequence which has undergone one or more conservative amino acid substitutions or side chain modifications.

Preferably the mammal is in need of such treatment, although the peptide may be administered in a prophylactic sense.

As will be readily appreciated by those skilled in the art, the route of administration and the nature of the pharmaceutically acceptable carrier will depend on the nature of the condition and the mammal to be treated. It is believed that the choice of a particular carrier or delivery system, and route of administration could be readily determined by a person skilled in the art. In the preparation of any formulation containing the peptide actives care should be taken to ensure that the activity of the peptide is not destroyed in the process and that the peptide is able to reach its site of action without being destroyed. In some circumstances it may be necessary to protect the peptide by means known in the art, such as, for example, micro encapsulation. Similarly the route of administration chosen should be such that the peptide reaches its site of action.

The pharmaceutical forms suitable for injectable use include sterile injectable solutions or dispersions, and sterile powders for the extemporaneous preparation of sterile injectable solutions. They should be stable under the conditions of manufacture and storage and may be preserved against oxidation and the contaminating action of microorganisms such as bacteria or fungi.

Those skilled in the art may readily determine appropriate formulations for the peptides or modified peptides of the present invention using conventional approaches. Identification of preferred pH ranges and suitable excipients, for example antioxidants, is routine in the art (see for example Cleland et al, 1993). Buffer systems are routinely used to provide pH values of a desired range and include carboxylic acid buffers for example acetate, citrate, lactate and succinate. A variety of antioxidants are available for such formulations including phenolic compounds such as BHT or vitamin E, reducing agents such as methionine or sulphite, and metal chelators such as EDTA.

The solvent or dispersion medium for the injectable solution or dispersion may contain any of the conventional solvent or carrier systems for peptide actives, and may contain, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about where necessary by the inclusion of various antibacterial and antifungal agents, for example, parabens, chlorobutanol, phenol, sorbic acid, thimerosal and the like. In many cases, it will be preferable to include agents to adjust osmolality, for example, sugars or sodium chloride. Preferably, the formulation for injection will be isotonic with blood. Prolonged absorption of the injectable compositions can be brought about by the use in the compositions of agents delaying absorption, for example, aluminum monostearate and gelatin. Pharmaceutical forms suitable for injectable use may be delivered by any appropriate route including intravenous, intramuscular, intracerebral, intrathecal, epidural injection or infusion.

Sterile injectable solutions are prepared by incorporating the active compounds in the required amount in the appropriate solvent with various of the other ingredients such as these enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, preferred methods of preparation are vacuum drying or freeze-drying a of a previously sterile-filtered solution of the active ingredient plus any additional desired ingredients.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations preferably contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained.

The tablets, troches, pills, capsules and the like may also contain the components as listed hereafter: A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

The present invention also extends to any other forms suitable for administration, for example topical application such as creams, lotions and gels, or compositions suitable for inhalation or intranasal delivery, for example solutions or dry powders.

Parenteral dosage forms are preferred, including those suitable for intravenous, intrathecal, intracerebral or epidural delivery.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form. A unit dosage form can, for example, contain the principal active compound in amounts ranging from 0.25 μg to about 2000 mg. Expressed in proportions, the active compound is generally present in from about 0.25 μg to about 200 mg/ml of carrier. In the case of compositions containing supplementary active ingredients, the dosages are determined by reference to the usual dose and manner of administration of the said ingredients.

In order to facilitate an understanding of the invention reference will be made to the examples and figure which illustrate some preferred embodiments of the invention. However it is to be understood the generality of the preceding description is not to be superseded by the particularity of the following description.

BRIEF DESCRIPTION OF THE DRAWINGS

FIG. 1 is an example of a nucleic acid sequence encoding CVID. The amino acid sequence including the leader sequence and terminal glycine is also shown. The nucleic acid sequence and amino acid sequence are also shown as SEQ ID NO: 12 and SEQ ID NO: 13 respectively, while the nucleic acid encoding the fourth loop is shown in SEQ ID NO: 11. The primary nucleotide sequence is 382 bp in length and comprises the leader sequence (amino acid residues 1 to 45), the mature peptide (amino acid residues 46 to 73 and boxed), the 3' untranslated region (depicted by lower case lettering immediately following the region of the mature peptide), and a small portion of the 5' untranslated region that was incorporated into the CSRD-301A primer (depicted in bold italicised lower case lettering at the start of the sequence). The start and stop codons delineating the peptide coding region are underlined. The putative amino acid sequences for the leader and mature peptides have been translated an from the primary nucleotide sequence and are shown in single letter abbreviation below the nucleotide sequence. The numbering above the nucleotide sequence relates to the position of the amino acid residues taken from the start codon. The position of the CSRD-301A PCR C 10 primer within the CVID sequence is highlighted in bold and italicised: the ANCHOR primer would be positioned immediately 3' to the poly-A tail (at 382+bp). An arrow at the arginine residue at position 45 indicates the most probable site for enzymatic cleavage of the leader peptide from the mature peptide.

The terminal glycine of the predicted expressed protein is removed by some form of post translational modification to leave an amidated C-terminal cystine in the protein isolated from snails.

EXAMPLES

Example 1

Assay guided fractionation of the venom of Conus catus was performed as follows:

The omega conotoxin CVID (1) was isolated originally from the crude venom extracted from the venom ducts of Conus catus collected from the Great Barrier Reef, Australia. Using gradient reverse phase HPLC the crude venom was separated into a number of fractions and these fractions then assayed in a $^{125}$I GVIA binding assay (see Example 4). Fractions active in the binding assay were further purified by assay-guided reverse phase HPLC and the primary structure obtained unambiguously by Edman sequencing. The fraction corresponding to CVID had a retention time of around 25–27 minutes.

The reverse phase HPLC was conducted on a Waters 600 HPLC system on preparative and analytical YYDAC C18 columns. Samples were typically run using a 1% gradient (100% A, 5 min; 100% A to 60% B, 60 min) at 1 ml/min and monitored at 214 nm. Additional fractionation was at times achieved using size-exclusion HPLC. Fractions for assay were collected either at 1 minute intervals or to correspond to peaks detected with a u. v. detector. The buffer system used for all analysis was A=0.1% TFA in $H_2O$ and B=0.09% TFA, 10% $H_2O$, 90% $CH_3CN$.

Example 2

The synthesis of peptides was performed according to the following procedures.

Materials and Methods

Materials

Synthesis of C-terminal amidated peptides was conducted on p-MBHA resin, obtained from Peninsula Laboratories and Peptide Institute, substitution values ranged from 0.66 to 0.93 meq/g. C-terminal acids were synthesised on Boc protected PAM resins obtained from Applied Biosystems. Boc protected amino acids were obtained from Peptide Institute, BA Chem, Nova Biochem, Fluka, Biosearch and Auspep. The side-chain protection chosen for the boc amino acids was Arg(Tos), Asn(Xan), Asp(OcHex), His(DNP), Lys(CIZ), Thr(Bzl), Tyr(BrZ), Glu(OcHex), Ser(Bzl), HyP (Bzl), Trp(CHO), Cys(p-MeBzl), Gln(Xan). All other Boc amino acids used were side-chain unprotected. DMF, DCM, DIEA, TFA, dicyclohexylcarbodiimide and hydroxybenzotriazole were all peptide synthesis grade from Auspep (Melbourne, Australia). Acetonitrile and methanol (Hipersolve-Far UV grade) were from BDH (Poole, UK). Water was obtained from a tandem Millipore Milli-RO–Milli-Q system. p-cresol and p-thiocresol were from Fluka (Germany). HF was supplied by BOC Gases (Brisbane, Australia). Ammonium acetate (AR) and ammonium sulphate (AR) were from AJAX Chemicals (Australia). Guanidine. HCl (99%+) and reduced and oxidised Glutathione were from Sigma Aldrich (USA).

Methods

Synthesis

Automatic peptide synthesis was conducted on an Applied Biosystems 430 A synthesiser, using symmetric anhydride or active ester chemistries to couple Boc-protected amino acids to the resin. Manual stepwise synthesis was conducted using BOC chemistry methodology, where 2 mmol of each amino acid is activated using 4 ml of 0.5 M HBTU in DMF and 470 μl DIEA, and in-situ coupling takes on average 10 min to obtain>99% coupling by quantitative ninhydrin$^2$ analysis. Both methods involved starting from p-MeBHA or PAM resin (0.5 mmol scale). Where —$OCH_2$—PAM resin was used the first amino acid was on the resin. Removal of the Boc protecting group prior to coupling was accomplished by vortexing or shaking in 100% TFA. DMF was used for flow washes and as the coupling solvent. Each residue (2 mmol) was routinely double coupled on the synthesiser and in the manual synthesis when ninhydrin values indicated less than 99% coupling. If coupling remained less than 99%, the remaining amino groups were acetylated using acetic anhydride in DMF (87 μl/ml).

Deprotection and Cleavage

For peptides containing histidine-DNP, the fully protected peptide was first subjected to thiolysis (20%

β-mercaptoethanol, 10% DIEA in DMF, 2×30 min), to remove the side-chain protection. The N-α-Boc group was then removed (TFA, 2×1 min), and for peptides containing tryptophan-CHO, deformylation was performed using a solution of ethanolamine (1.5 g) in 25 ml 5% water in DMF (2×30 min). The peptide was washed with DCM and dried under nitrogen. Cleavage from the resin and simultaneous deprotection of side-chains was carried out in liquefied HF in the presence of the scavengers p-cresol and p-thiocresol (18:1:1 by volume) at −5–5° C. for 1.5 hr. HF was removed under vacuum, the peptide was precipitated with cold ether, collected by filtration on a sintered funnel and washed with cold ether to remove scavenger adducts. The peptide was dissolved in either 50% AcOH or 45% aqueous acetonitrile, diluted with water and lyophilised.

Folding and Oxidation

Purified reduced peptides were oxidised at a concentration of 0.02 to 0.05 mM in either aqueous 0.33M $NH_4OAc$/0.5M GnHCl, or aqueous 2M $(NH_4)_2SO_4$/0.1M NH4OAc with pH adjusted to 7.5–8.0 using 0.01M $NH_4OH$ The solution was stirred for 3 to 5 days at 4° C., in the presence of reduced and oxidised glutathione (molar ratio of peptide:GSH:GSSG was 1:100:10). The reaction mixtures were sampled periodically and analysed by RP—HPLC and eluant fractions were collected for electrospray mass spectrometric analysis. When LC and MS confirmed that oxidation was complete, the oxidation was terminated by lowering the pH to 2–3 with TFA.

Chromatographic Analysis and Purification

A WATERS 600 HPLC system equipped with an auto-injector was used for all RP-HPLC. Analytical RP-HPLC was conducted on a WATERS Delta pak C18, 300A (0.39× 30 cm) column or a VYDAC C18, 5μ (0.46×25 cm) column. Samples were run using a 1% gradient (100% A, 5 min; 100% A to 60% B, 60 min), at 1 ml/min and monitored at 214 nm. The buffer system used for all analysis was A=0.1% TFA in $H_2O$ and B=0.09% TFA, 10% $H_2O$, 90% $CH_3CN$.

A VYDAC C18, 5μ (1.0×25 cm) column was used for semipreparative RP-HPLC and a VYDAC C18, 10μ (2.2×25 cm) column was used for preparative RP-HPLC. The crude reduced peptides were purified by preparative chromatography, using a 1% gradient (100% A to 80% B, 80 min) with a flow rate of 8 ml/min and u. v detection at 230 nm. Fractions were collected and analysed by electrospray mass spectrometry. Fractions which gave the desired mass were then analysed by analytical RP-HPLC to confirm purity, and those fractions which were pure were combined and lyophilised to give the reduced peptide. Oxidised peptides were purified by loading the acidified reaction mixtures onto a preparative column at a flow rate of 8 ml/min, washing through with 100% A until all oxidation buffer had eluted and then applying a 1% gradient (100%A to 80% B, 80 min) with a flow rate of 8 ml/min and u.v detection at 230 nm. Fractions were collected and analysed as for the reduced peptides. If further purification was necessary the peptide was repurified on a semipreparative column on a 1% gradient (100 A to 80% B, 80 min) with a flow rate of 3 ml/min and u.v detection at 230 nm. Fractions were collected and analysed as before.

Mass Spectrometry

Mass spectra were measured on a PE SCIEX API-III triple quadrupole Ion Spray mass spectrometer. Data was obtained in the positive ion mode by the accumulation of data in the range 400–2100 amu from several scans using a scan step of 0.1 amu, and a delay time of 0.3 s.

Peptides were dissolved at a concentration of 1 mg/ml in 45% aqueous acetonitrile containing 0.1% TFA. HPLC fractions were used without further treatment. Samples were delivered to the orifice via a glass capillary by direct injection (5–20 ul) using a Rheodyne injector into a 30–40 ul/min solvent flow of 50% aqueous acetonitrile containing 0.05% TFA. The resultant data was subjected to deconvolution (Hypermass-MacSpec 3.2, SCIEX, Canada) to determine the Mr of the observed protonated species.

Other high-resolution data were obtained on a BRUKER Spectrospin BioAPEX external-ion-source Fourier transform electrospray mass spectrometer at a magnetic field of 4.7 T.

Data for some of the peptides synthesised is tabulated below

TABLE 3

List of synthesised peptides, optimal yields and Mass values.

| PEPTIDE | REDUCED YIELD % | OXIDISED YIELD % | EXPECTED MASS (Mr, Da) | OBSERVED MASS (Mr, Da) |
|---|---|---|---|---|
| CVD | 36 | 35 | 2755 | 2755 |
| $R^{10}$-CVID | 36 | 40 | 2784 | 2784 |
| $D^9R^{10}$-CVID | 33 | 29 | 2812 | 2812 |

Example 3

Isolation and Characterisation of the CVID Gene Sequence

RNA extraction and cDNA synthesis

Two specimens of *Conus catus* were collected from Lady Elliot Island on the Queensland Great Barrier Reef The animals were anaethesised on ice, and dissected to remove the, venom duct in a region from the venom bulb to the proboscis. The ducts were sectioned, placed in a buffer containing guanidinium thiocyanate/N-lauroyl sarcosine, then emulsified with manual grinding. Poly-A tailed mRNA was extracted from the mixtures using the Pharmacia Biotech QuickPrep mRNA purification system.

Strand-1 cDNA was 3' end synthesised from the C. *catus* poly-A mRNA templates using a Not1-d(T)$_{18}$ bifunctional primer (5'-AACTGGAAGAATTCGCGGCCGCAGGAAT$_{(18)}$-3')[SEQ ID NO:40] (Pharmacia Biotech) in conjunction with Superscript II reverse transcriptase (Gibco BRL). The resultant cDNA templates were used to manufacture double stranded cDNA using a RNaseH/DNA polymerase procedure as per the Pharmacia Biotech cDNA Timesaver protocol. MARATHON (Clontech) adaptors were then added to the 5' and 3' ends of the ds-cDNA molecules to complete the cDNA construction. A representation of a complete coneshell venom peptide cDNA molecule is shown in FIG. 1.

PCR derivation of CVID and related cDNA sequences

PCR was carried out on samples containing ds-cDNA from C. *catus*, the CSRD-301A primer (5'-ATCATCAAAATGAAACTGACGTC-3') [SEQ ID NO: 41], the ANCHOR primer (5'-AACTGGAAGAATTCGCGGCCGCAGGAAT-3') [SEQ ID NO: 42] and an appropriate Taq polymerase (Biotech International) and buffer (25 mM Mg, 100 uM deoxynucleotides, buffered at pH 8.5) in a thermal cycler (Omnigene) at 95° C./2 mins for 1 cycle, 95°C./30 sec–55° C./60 sec–720C/90 sec for 35 cycles, and 72°C./10 mins for 1 cycle. This PCR produced a heterogeneous DNA product of approximately 380 bp to 500 bp. Sequence analysis of clones derived from this PCR product have shown it to contain the sequence CVID as well as other related venom peptide sequences.

Cloning and sequencing of CVID

The DNA product produced from the CSRD-301A-ANCHOR driven PCR of C. *catus* cDNA was electrophoresed in low melting point agarose and excised. The DNA was extracted from the agarose on Qiagen columns, rephosphorylated with T4 DNA kinase (Progen), blunt ended with Klenow polymerase (Progen), and ligated with T4 DNA ligase (Progen) into the multiple cloning site of dephosphorylated Sma-1 cut pUC-18 plasmid vector DNA (Pharmacia Biotech). The vector DNA was electrotransformed into Bluescript *E. coli* cells, to produce a library of clones representing the PCR product. Aliquots of the library were plated onto $LB_{amp}$ plates, and individual clones selected and propagated overnight in $TB_{amp}$ broth. Plasmid DNA was purified from the culture using the RPM system (BIO 101), and the PCR DNA inserts within the vector sequenced using the pUC-18 forward and reverse primers (Pharmacia Biotech), dideoxy terminator sequencing chemistries (Perkin Elmer) on ABI 373 sequencers. The sequence data was analysed using SEQUENCE NAVIGATOR software (Applied Biosystems).

CVID gene sequence

Clone number Cca-6 within the C catus CSRD-301A/ANCHOR venom duct cDNA PCR library provided the sequence for the CVID peptide. The nucleotide sequence and the anticipated translation of the associated amino acid sequence for the CVID gene are shown in FIG. 1. Further analysis of this clone library revealed a total of eight clones with identical sequence. All clones were sequenced in both orientations to produce a consensus sequence.

The CVID sequence has the following characteristics:

A coding sequence of 222 base pairs which translates to 73 amino acids

A predicted mature peptide sequence of 28 amino acids. It should be noted that in the protein isolated from snails the terminal glycine of the predicted expressed protein is removed by some form of post translational modification to leave an amidated C-terminal cystine.

The predicted mature peptide has a six cysteine framework in the pattern of; C-$a_6$-C-$a_6$-CC-$a_3$-C-$a_6$-C The nucleotide and amino acid sequence of both the leader peptide and the mature peptide are not identical to any known peptide sequence.

Further experiments on C. *catus* similar to that described above were undertaken using some additional primers in place of the CSRD-301A primer. These primers were designed to be more specific and were OM-2A (5'-ATC AAA ATG AAA CTG ACG TGT GTG GTG-3') [SEQ ID NO: 43] and Cca-6-3B (S-GCG TTT TGA TCA GCC ACA TCT ACC TA-3') [SEQ ID NO: 44]. These experiments led to identification of sequences for some of the derivatives of CVID.

Example 4

Radioligand Binding Assays

Preparation of $^{125}$I-GVIA and $^{125}$I-MVIIC

Peptides were iodinated using IODO-GEN® (Fraker P. J. et al., 1978) (1, 3, 4, 6-tetrachloro-2*a,* 6*a*-diphenylglycuoluril) [Ahmad S. N. et al., 1988, Cruz L. J. et al., 1986], 5 µl (5.75 mg/ml, 17.4 mCi/mg) Na$^{125}$I (DuPont NEN®, New research products, Boston) and 25 ol of sodium phosphate buffer (50 mM, pH 7.4) were added to an eppendorf tube coated with IODO-GEN® (Pierce, Rockford, USA) and incubated for 5 mins. The reaction mixture was vortexed and transferred to an eppendorf tube containing 10 µl of the peptide of interest This mixture was then allowed to react for another 5 min prior to purification by HPLC.

Preparative HPLC of $^{125}$I-labelled peptides was performed on a Waters 680 gradient controller equipped with two WATERS 510 HPLC pumps and a WATERS 481 absorbence detector. Peptides were analysed on VYDAC reverse phase C-18 analytical column (4.6×250 mm) eluted at 1 ml/min with a linear gradient of 0–67% of solvent B over 100 min: solvent A, 1% TFA (trifluoroacetic acid); solvent B, 90% ACN+0.09% TFA. Separation was monitored at 214 nm and 1 ml fractions were collected. Fractions of interest were detected with a LKB Wallac 1272 automatic Gamma counter.

To confirm the identity of iodinated peptides, mass spectrometry was preformed on a PE-SCIEX API III mass spectrometer (PESciex, Thornhill, Ontario, Canada). HPLC fractions from peptides iodinated with non-radioactive K$^{127}$I were injected directly into the mass spectrometer. Mass spectra were acquired on a Apple Macintosh IIfx computer using the software package MacSpec (Sciex, Toronto).

Rat Membrane Preparation

Rat membrane was prepared according to the procedure of Wagner et al. (1988). Rats were sacrificed by cervical dislocation and their brains removed and immediately frozen in liquid nitrogen. Frozen brains were stored at −78° C. until required. Three brains (wet weight, 6.25 g) were thawed and homogenised with ULTRATURREX homogenizer (IKA, 170 Watt) in 125 ml 50 mM HEPES pH 7.4. Homogenised brain was centrifuged at 16000 rpm (35000g) for 20 min at 4° C. and the supernatant discarded. The pellet was resuspended by further homogenisation in 50 mM HEPES, pH 7.4, 10 mM EDTA and incubated at 4° C. for 30 min. Centrifugation was repeated as above and the supernatant discarded. The pellet was resuspended in 125 ml 50 mM HEPES, pH 7.4 (1:20 dilution) and stored at −78° C.

Binding Assays

Binding experiments were performed as previously described (Kristipati et al., 1994, Nadasdi et al., 1995). Ligand binding assays were run in triplicate in glass tubes at room temperature. Briefly, assays were performed in 12×75 mm borasilicate culture tubes at room temperature and incubated for 1 hr. Each tube contained 100 µl each of test compound, iodinated ligand (7 fmol) and rat membrane (16 mg) added in this order. The assay buffer contained 20 mM HEPES pH 7.2, 75 mM NaCl, 0.1 mM EDTA, 0.1 mM EGTA, 0.1% BSA and protease inhibitors, 2 mM leupeptin and 0.5 U aprotinin. The nonspecific binding was determined in the presence of either 17 nM GVIA or 100 nM MVIIC. Assays were terminated by vacuum filtration on a Millipore manifold filtration system using glass fibre filters (Whatman GFB) presoaked in 0.6% polyethylenimine. Each tube was washed 3 times with 3 ml ice-cold wash buffer (20 mM HEPES pH 7.2, 125 mM NaCl and 0.1% BSA). Filters were counted on a gamma counter. In some instances, potency estimates at the N-type calcium channel were determined by measuring $^{125}$I-GVIA bound to rat brain membrane that was filtered using a Tomtec harvester and counted with a MICROBETA Jet scintillation counter. Similar results were obtained with both procedures. In all cases the GRAPHAD PRISM program was used to generate binding curves and calculate $EC_{50}$ values. Values for some of the compounds of the present invention are shown in Table 4.

TABLE 4

$EC_{50}$ in rat brain binding assays

| PEPTIDE | $^{125}$I GVIA Assay | $^{125}$I MVIIC Assay |
|---|---|---|
| CVID □ | $3.1e^{-11}$ ($2.3e^{-10}$) | $7.1e^{-5}$ ($6.4e^{-5}$) |
| $R^{10}$-CVID | $7.5e^{-11}$ ($5.3e^{-11}$) | $<3.5e^{-6}$ ($1.2e^{-3}$) |
| $D^9R^{10}$-CVID | $1.8e^{-9}$ ($7.6e^{-10}$) | $<4.6e^{-5}$ ($<1.0e^{-3}$) |
| (4) | $3.2e^{-11}$ | $<6.3e^{-7}$ |
| (5) | $2.15e^{-11}$ | $<7.1e^{-7}$ |
| (7) | $4.3e^{-11}$ | $<5.6e^{-7}$ |
| (11) | $4.57e^{-11}$ | $<4.3e^{-6}$ |
| (12) | $7.11e^{-11}$ | $<4e^{-6}$ |
| (13) | $5.03e^{-11}$ | $<4e^{-6}$ |
| (14) | $7.1e^{-10}$ | $<4.7e^{-6}$ |
| (15) | $4.4e^{-10}$ | $<4.6e^{-6}$ |
| (18) | $1.7e^{-10}$ | $<1.4e^{-6}$ |
| (20) | $3.5e^{-11}$ | $<3.4e^{-7}$ |
| (21) | $9.1e^{-11}$ | $<7.4e^{-7}$ |

Where two figures are quoted, the data in brackets represents data from initial binding studies while the other figure represents results obtained from further experiments.

Example 5

In view of the high level of selectivity shown by CVID for N-type VSCC, the structural features that might contribute to its N-type selectivity were investigated. This was done using standard $^1$H NMR techniques of the type known to those skilled in the art.

Methods $^1$H NMR Structure Studies $^1$H NMR spectroscopy-All NMR experiments were recorded on a Bruker ARX 500 spectrometer equipped with a z-gradient unit or on a Bruker DMX 750 spectrometer equipped with a x, y, z-gradient unit. Peptide concentrations were in the range 1–5 mM. Each analogue was examined in 95% $H_2O$/5% $D_2O$ (pH 2.5–3.5). $^1$H NMR experiments recorded were NOESY (Kumar et al., Jeener et al) with mixing times of 200 and 400 ms, and TOCSY (Bax) with a mixing time of 120 ms. All spectra were recorded at 293° K and were run over 6024 Hz (500 MHZ) or 8192 Hz (750 MHZ) with 4K data points, 400–512 FIDs, 16–64 scans, and a recycle delay of 1 s. Extra experiments recorded for CVID included NOESY (100 ms mixing time), DQF-COSY (Rance), and E-COSY (Greisinger)(100% $D_2O$) at 293° K, and duplicate experiments at 280' K.

Solvent was suppressed using the WATERGATE sequence (Piotto et al., 1992) and spectra processed using UXNMR. FIDs were multiplied by a polynomial function and apodised using a 90° shifted sine-bell function in both dimensions, or a mild Gaussian function in $f_1$ prior to Fourier transformation. Baseline correction using a $5^{th}$ order polynomial was applied and chemical shift values were referenced internally to DSS at 0.00 ppm. Secondary Hα shifts were measured using the random coil shift values of Marutka et al., (1995).

$^3J_{NH-H\alpha}$ coupling constants were measured from high resolution 1 D spectra (32 K) and compared to those obtained from the DQF-COSY spectra which were strip transformed to 8 K×1 K and extracted using the Lorentzian line-fitting routine in the program Aurelia (Bruker GMBH). $^3J_{H\alpha-H\beta}$ coupling constants were measured directly from the E-COSY spectra transformed to high digital resolution (8 K×1 K).

Distance restraints and structure calculations-Peak volumes in NOESY spectra were classified as strong, medium, weak, and very weak corresponding to upper bounds on interproton distances of 2.7, 3.5, 5.0, and 6.0 Å, respectively. Lower distance bounds were set to 1.8 Å. Appropriate pseudoatom corrections were made (Wüthrich et al., 1983) and distances of 0.5 Å and 2.0 Å were added to the upper limits of restraints involving methyl and phenyl protons, respectively. $^3J_{NH-H\alpha}$ coupling constants were used to determine φ dihedral angle restraints [Pardi et al., 1984] and $^3J_{H\alpha-H\beta}$ coupling constants, together with relevant NOESY peak strengths, were used to determine $_\chi$1 dihedral angle restraints [Wagner et al., 1987]. Where there was no diastereospecific assignment for a prochiral pair of protons, the largest upper bound for the two restraints was used but where stereospecific assignments a were established, the distances were specified explicitly.

Structures were calculated using the torsion angle dynamics/simulated annealing protocol in XPLOR version 3.8 [Brünger et al., 1986; Brünger, 1992; Rice; Stein] using a geometric forcefield based on Engh and Huber parameters (Brooks et al., 1983). Starting structures were generated de novo using random (φ, ι) dihedral angles and energy minimised (500 steps) to produce structures with correct local geometry. The structures were subjected to a total of 15 ps of high temperature (50 000° K) molecular dynamics before cooling over 15 ps to 0° K and final energy minimisation (1000 steps). Structure refinements were performed using energy minimisation (1000 steps) under the influence of a modified Engh and Huber forcefield.

Data analysis-Structures were compared using pairwise and average RMSDs for the Cα, C and N atoms (XPLOR version 3.8), and by calculating angular order parameters for the backbone dihedral angles [Hyberts et al., 1992; Pallaghy et al., 1993]. Structure visualisation was performed using the INSIGHTII program (MSI).

RESULTS $^1$H NMR Spectroscopy

The greatest difference in Hα secondary shifts compared to MVIIA was seen in loops 2 and 4 of CVID. Differences in loop 4 are not surprising given that CVID has a novel sequence and incorporates two additional residues, the differences in loop 2 are noteworthy since loop 2 in MVIIA and CVID are similar. The secondary shifts of residues 9–14 in CVID follow the same basic pattern of those in MVIIA, but are of greater magnitude, indicating that the structure of loop 2 in CVID may be more stabilised. This could stem from a long range interaction with loop 4. Loop 2 has previously been the least defined region of ω-conopeptide structure, with residues of this loop characterized by relatively broad peaks in the $^1$H NMR spectra, indicative of conformational exchange (Nielsen et al., 1996; Lew et al., 1997). This lack of structure definition has hindered attempts to understand the crucial role loop 2 plays in activity, function, and selectivity of ω-conopeptides, particularly that of the important binding determinant Tyr13, as well as residues of secondary importance such as Leu11 and Arg10 in MVIIA (Nadasdi et al., 1995). Thus CVIID may provide a novel structural template for pharmacophore development. Since the significant differences in secondary Hα shifts for residues in loops 2 and 4 in CVIID precluded accurate modelling of CVID from existing ω-conotoxins structures, and given its enhanced N-type selectivity, the 3D structure of CVID was determined using $^1$H NMR spectroscopy, as described below.

3D Structure of conopeptide CVID

A set of 50 structures of CVID were calculated based a total of 481 distance restraints derived from 159 intraresidue, 110 sequential, 184 medium and long-range NOEs, 28 H-bond restraints defining a total of 14 H-bonds and 23 φ and 10 χI dihedral angle restraints. A total of 47 structures converged to a consensus fold, with no NOE violation greater than 2 Å, and no dihedral violations greater than 3°. Of these, the 20 lowest energy structures were chosen to represent the structure of CVID. The structures are exceptionally well defined, with a backbone pairwise RMSD of 0.35 Å (calculated over all residues). The angular order parameters (S) for the φ and ι backbone dihedral angles averaged 0.99, indicating a high degree of structure precision that is reflected in the low the average RMSDs to the mean structure of 0.24 Å.

Novel features in CVID that have not been described for other co-conotoxins include the presence of two hydrogen bonds between loops 2 and 4, from the NH protons of Lys10 and Leu11 to the C=O oxygen atoms of Gly22 and Thr23, respectively. It is possible that these hydrogen bonds enhance the stability of loop 2 in CVID compared with other conotoxins. Importantly, the backbone of Tyr13 has been stabilized in a $\alpha_L$ conformation, with the χI sidechain torsion angle at −60'. Attempts to define the conformation of Tyr3 in other ω-conotoxins have been ambiguous, and indeed Tyr13 may adopt an averaged conformation in other conotoxins. The structural observations for the conformation of Tyr13 in CVID are supported by the presence of a strong intraresidue $NH_i$—$H\alpha_i$ NOE, together with a weaker $H\alpha_{i-1}$—$NH_i$ and a $^3J_{NH-H\alpha}$ coupling constant of 7 Hz.

Discussion

CVID was found to adopt a similar global fold to the known (conotoxins such as MVIIA, MVIIC and GVIA. This comparison also highlights significant differences in the structure of loop 4, which is oriented downwards in MVIIA (with the shortest loop 4) and MVIIC, outwards in GVIA, but curves towards loop 2 in CVID to create a more globular surface. The presence of two hydrogen bonds between loop 4 and loop 2 in CVID is likely to favour loop 4 in this orientation, and help stabilize loop 2. This is an interesting finding, as hydrogen bonds between loops 2 and 4 have not been reported previously for GVIA, MVIIA or MVIIC. This unique aspect of CVID structure may contribute to its improved selectivity for the N-type VSCC, and suggest that the loop 2/4 combination may contain important determinants for ω-conopeptide selectivity.

The high potency and selectivity of CVID make it an attractive candidate for pharmocophore development based on its 3D structure. The improved stability of loop 2 may contribute entropically to its superior selectivity over other ω-conotoxins found to date. However, lacking the important secondary binding residues present in loop 4 of MVIIA (Arg21, Nadasdi et al., 1995) and GVIA (Lys24, Tyr22; Lew et al., 1997) it is likely that a unique set of ω-conotoxin/VSCC interactions originate from loop 4 in CVID, possibly through the relatively exposed Thr23 or Val24.

References

Ahmad, S. N., et al., (1988) Brain Res., 453, 247–56.
Bvax, A., and Davis, D. G., (1985)*J. Magn. Reson.,* 65, 355–60.
Brooks, B., Brucoli, R., Olafson, B. O., States, D., Swaminathan, S., and Karplus, M. (1983) *J. Comput. Chem.* 4, 187–217.
Brünger, A. T., Clore, G. M., Gronenborn, A. M, and Karplus, M. (1986) *Proc. Nat. Acad. Sci.,* U.S.A 83, 3801–3805.
Brünger, A. T. (1992) X-PLOR version 3.1. A System for X-ray Crystallography and NMR Yale University, New Haven, Conn.
Cabot P. J., Cramond T. R, and Smith M T (1998), *Pul. Pharmacol. Ther.,* 10(4), 215–221.
Cleland et al., *Crit Rev. Therap. Drug Carr, Syst.,* (1993), 10, 307–366.
Cruz, L. J., et al., (1986) *J. Biol. Chem.,* 261, 6230–6233.
Drugs of the Future, (1994), 19(2), 128.
Drugs of the Future, (1998), 23(2), 152.
Drug Data Report, (1993), 15(9), 807.
Fraker, P. J. et al., (1978) *Biochem. Biophys. Res. Commun* 80, 849–857.
Greisinger, C., Sorenson, O. W., and Ernst, R. R. (1987). *J. Magn. Reson.* 75, 474–492.
Heading C., (1999), *Curr. Opin. CPNS Investigational Drugs,* (1999), 1(1), 153–166.
Hyberts, S. G., Goldberg, M. S., Havel, T. S., and Wagner, G. (1992)*Protein Sci.* 1, 736–751.
Jeener, J., Meier, B. H., Bachmann P., and Ernst, R. R. (1979) *J. Chem. Phys* 71, 4546–4553.
Kim, J. et al., (1995) *Biochem. Biophys. Res. Commun.* 214, 305–309.
Kristipati R. et al., Molecular and Cellular Neurosciences, 5, 219–228 (1994).
Kumar, A., Ernst, R. R, and Wüthrich, K (1980) *Biochem. Biophys. Res. Commun.* 95, 1–6.
Lew, M. et al., (1997)*J. Biol. Chem.,* 272, 12014–12023.
M. Schnoltzer, et al., *Int. J. Peptide Protein Res.* 40, 180 (1992).
Nadasdi, L. et al., (1995) *Biochemistry* 34, 8076–8081.
Omote K. et ai., (1996) Anesthesiology, 84, 636–43.
Malmberg A. B., and Yaksh T. L., (1995) *J Neurosci.,* 14, 4882–90.
Marutka, G., Dyson, H. J., and Wright, P. E. (1995) *J. Biolmol. A* 5, 14–24.
Nielsen, K J., Skjaerbaek, N., Dooley, M., Adams, D. A., Mortensen, M., Dodd., P., Craik,
D. J., Alewood, P. F., and Lewis, R. J. (1999) *J. Med. Chem.* 42, 415–426.
Nielsen, K. J., Thomas, L., Lewis, R. J., Alewood, P. F., and Craik., D. J. (1996). *J. Mol. Biol.* 263, 297–310.
Pallaghy, P. K., Duggan, B. M., Pennington, M. W., and Norton, R. S. (1993) *J. Mol. Biol.* 234, 405–420.
Pardi, A, Billeter, M., and Wüthrich, K. (1994) *J Mol. Biol.* 180, 741–751.
Piotto, M., Saudek, V., and Sklenár, V. (1992) *J. Biolmol. NMR* 2, 661–665.
Rance, M., Sorenson, O. W., Bodenhauser, G., Wagner, G., Ernst, R. R., and Wüthrich, K. (1983) *Biochem. Biophys. Res. Commun.* 177, 479–485.
Ray, N. J., A. J. Jones and P. Keen, (1991), *Br. J. Pharmacol.* 102797–800.
Rice, L. M., and Brunger, A. T. (1994) *Proteins: Struct. Funct. Genet.* 19, 277–290.
Sarin V. K. et al., *Anal. Biochem* 117, 147 (1981).
Sato, K et al., (1997) FEBS Letters 414, 480–484.
Stein, E. G., Rice, L. M., and Brunger, A. T. (1996) *J. Magn. Reson* 124, 1554–1564.
Wagner, G., Braun, W., Havel, T. F., Schaumann, T., Go, N., and Wüthrich, K. (1987) *J. Mol. Biol.* 196, 611–639.
Wagner, J. 3A, et al., (1988) J. Neurosci., 8, 3354–9.
White D. M. and Cousins M. *J., Brain Research,* (1998), 801, 50–58.
Wüthrich, K., Billeter, M., and Braun, W. (1983) *J. Mol. Biol* 169, 949–961.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

What is claimed is:

1. An isolated, synthetic or recombinant ω-conotoxin peptide in which the fourth loop between cysteine residues 5 and 6 comprises the following sequence of amino acids:
SGTVGR [SEQ ID NO: 1].

2. An isolated, synthetic or recombinant ω-conotoxin peptide according to claim 1 wherein each of the first, second and third loops of the ω-conotoxin peptide corresponds to the loop of a naturally occurring ω-conotoxin peptide, or such a sequence of amino acids which has undergone one or more amino acid substitutions, additions or deletions.

3. An isolated, synthetic or recombinant ω-conotoxin peptide according to claim 1 wherein the second loop is selected from the group consisting of:
SKLMYD [SEQ ID NO: 2],
SRLMYD [SEQ ID NO: 3],
DRLMYD [SEQ ID NO: 4],
DKLMYD [SEQ ID NO: 33],
SKLAYD [SEQ ID NO: 34],
SKLNleYD [SEQ ID NO: 35],
SPLNleYD [SEQ ID NO: 36], SKLOhmhserYD [SEQ ID NO: 37], and
SKLOmserYD [SEQ ID NO: 38].

4. An isolated, synthetic or recombinant ω-conotoxin peptide according to claim 1 having the following sequence:
CKSKGAKCSKLMYDCCSGSCSGTVGRC [SEQ ID NO: 5]
CKSKGAKCSRLMYDCCSGSCSGTVGRC [SEQ ID NO: 6]
CKSKGAKCDRLMYDCCSGSCSGTVGRC [SEQ ID NO: 7]
CRSKGAKCSKLMYDCCSGSCSGTVGRC [SEQ ID NO: 14]
CKSKGARCSKLMYDCCSGSCSGTVGRC [SEQ ID NO: 15]
CKSKGAQCSKLMYDCCSGSCSGTVGRC [SEQ ID NO: 16]
CKSKGAKCDKLMYDCCSGSCSGTVGRC [SEQ ID NO: 18]
CKYKGAKCSRLMYDCCSGSCSGTVGRC [SEQ ID NO: 19]
CKSKGAKCSKLAYDCCSGSCSGTVGRC [SEQ ID NO: 20]
CKSKGAKCSKLMYDCCTGSCSGTVGRC [SEQ ID NO: 21]
CKSKDalAKCSKLMYDCCSGSCSGTVGRC [SEQ ID NO: 22]
CKSKGAKCSKLMYDCCSGSCSGTVGRCY [SEQ ID NO: 23]
CKSKGAKCSKLMYDCCSGSCSGTVGRC [SEQ ID NO: 24]
YCKSKGAKCSKLMYDCCSGSCSGTVGRC [SEQ ID NO: 25]
CKSKGAKCSKLMYDCCSGSCSGTVGRC [SEQ ID NO: 26]
CKSKGAKCSKLNleYDCCSGSCSGTVGRC [SEQ ID NO: 27]
CKSKGAKCSRLNleYDCCSGSCSGTVGRC [SEQ ID NO: 28]
CKYKGAKCSRLNleYDCCSGSCSGTVGRC [SEQ ID NO: 29]
CKSKGAKCSKLOmhserYDCCSGSCSGTVGRC [SEQ ID NO: 30]
CKSKGAKCSKLOmserYDCCSGSCSGTVGRC [SEQ ID NO: 31]
CKSKGAKCSKLM(O)YDCCSGSCSGTVGRC [SEQ ID NO: 32].

5. An isolated, synthetic or recombinant ω-conotoxin peptide according to claim 4 having one of the following sequences:
CKSKGAKCSKLMYDCCSGSCSGTVGRC [SEQ ID NO: 5]
CRSKGAKCSKLMYDCCSGSCSGTVGRC [SEQ ID NO: 14]
CKSKGARCSKLMYDCCSGSCSGTVGRC [SEQ ID NO: 15]
CKSKGAKCSKLAYDCCSGSCSGTVGRC [SEQ ID NO: 20]
CKSKGAKCSKLNleYDCCSGSCSGTVGRC [SEQ ID NO: 27]
CKSKGAKCSRLNleYDCCSGSCSGTVGRC [SEQ ID NO: 28]
CKSKGAKCSKLOmhserYDCCSGSCSGTVGRC [SEQ ID NO: 30]
CKSKGAKCSKLOmserYDCCSGSCSGTVGRC [SEQ ID NO: 31].

6. An isolated, synthetic or recombinant ω-conotoxin peptide according to claim 1 having the following sequence:
CKSKGAKCSKLMYDCCSGSCSGTVGRC [SEQ ID NO: 5].

7. An isolated, synthetic or recombinant ω-conotoxin peptide according to claim 1 having a selectivity for N-type calcium channels over P/Q-type calcium channels.

8. A method of testing the calcium channel binding activity of a test peptide or compound, comprising (1) determining the level of binding of an isolated, synthetic or recombinant ω-conotoxin peptide according to claim 1 to calcium channels in the absence of said test peptide or compound, (2) determining the level of binding of said isolated, synthetic or recombinant ω-conotoxin peptide to calcium channels in the presence of said test peptide or compound, and (3) comparing the level determined in step (1) to the level determined in step (2).

9. A composition comprising: an isolated, synthetic or recombinant ω-conotoxin peptide in which the fourth loop between cysteine residues 5 and 6 comprises the following sequence of amino acids:
SGTVGR [SEQ ID NO: 1]
a pharmaceutically acceptable carrier or diluent.

10. A method for the treatment of conditions for which blockade of N-type calcium channels is associated with effective treatment including the step of administering to a mammal an effective amount of an isolated or recombinant ω-conotoxin peptide in which the fourth loop between cysteine residues 5 and 6 comprises the following sequence of amino acids:
SGTVGR [SEQ ID NO: 1].

11. A method for reducing neuronal damage following ischemia, for the production of analgesia, for enhancement of opiate analgesia, for the treatment of schizophrenia, hypertension, inflammation or diseases which cause bronchoconstriction, stimulant psychoses or for inhibition of progression of neuropathic pain including the step of administering to a mammal an effective amount of an isolated or recombinant ω-conotoxin peptide in which the fourth loop between cysteine residues 5 and 6 comprises the following sequence of amino acids:
SGTVGR [SEQ ID NO: 1].

12. A method of screening for identifying compounds which bind to N-type voltage sensitive calcium channels, comprising (1) determining the level of binding of an isolated, synthetic or recombinant ω-conotoxin peptide according to claim 1 to N-type voltage sensitive calcium channels in the absence of a test compound, (2) determining the level of binding of said isolated, synthetic or recombinant ω-conotoxin peptide to calcium channels in the presence of said test compound, and (3) comparing the level determined in step (1) to the level determined in step (2), thereby identifying compounds which bind to N-type voltage sensitive calcium channels.

13. An isolated recombinant or synthetic ω-conotoxin peptide, wherein said ω-conotoxin peptide binds to voltage sensitive calcium channels and comprises six Cysteine residues, wherein the fourth loop between cysteine residues 5 and 6 comprises the amino acid sequence as set forth in SEQ ID NO: 1, and wherein SEQ ID NO: 1 is directly adjacent to a cysteine at both its NH2 and the COOH terminus.

* * * * *

```
                         SEQUENCE LISTING

<160> NUMBER OF SEQ ID NOS: 44

<210> SEQ ID NO 1
<211> LENGTH: 6
<212> TYPE: PRT
<213> ORGANISM: conus catus

<400> SEQUENCE: 1

Ser Gly Thr Val Gly Arg
1               5

<210> SEQ ID NO 2
<211> LENGTH: 6
<212> TYPE: PRT
<213> ORGANISM: conus catus

<400> SEQUENCE: 2

Ser Lys Leu Met Tyr Asp
1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: A modified
      version of the second loop of CVID

<400> SEQUENCE: 3

Ser Arg Leu Met Tyr Asp
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: A modified
      version of the second loop of CVID

<400> SEQUENCE: 4

Asp Arg Leu Met Tyr Asp
1               5

<210> SEQ ID NO 5
<211> LENGTH: 27
<212> TYPE: PRT
<213> ORGANISM: conus catus

<400> SEQUENCE: 5

Cys Lys Ser Lys Gly Ala Lys Cys Ser Lys Leu Met Tyr Asp Cys Cys
1               5                   10                  15

Ser Gly Ser Cys Ser Gly Thr Val Gly Arg Cys
            20                  25

<210> SEQ ID NO 6
```

```
<211> LENGTH: 27
<212> TYPE: PRT
<213> ORGANISM: Artificial Sequence
<220> FEATURE:
<223> OTHER INFORMATION: Description of Artificial Sequence: A modified
      form of CVID

<400> SEQUENCE: 6

Cys Lys Ser Lys Gly Ala Lys Cys Ser Arg Leu Met Tyr Asp Cys Cys
1               5                   10                  15

Ser Gly Ser Cys Ser Gly Thr Val Gly Arg Cys
            20                  25

<210> SEQ ID NO 7
<211> LENGTH: 27
<212> TYPE: PRT
<213> ORGANISM: Artificial Sequence
<220> FEATURE:
<223> OTHER INFORMATION: Description of Artificial Sequence: A modified
      form of CVID

<400> SEQUENCE: 7

Cys Lys Ser Lys Gly Ala Lys Cys Asp Arg Leu Met Tyr Asp Cys Cys
1               5                   10                  15

Ser Gly Ser Cys Ser Gly Thr Val Gly Arg Cys
            20                  25

<210> SEQ ID NO 8
<211> LENGTH: 25
<212> TYPE: PRT
<213> ORGANISM: conus magus

<400> SEQUENCE: 8

Cys Lys Gly Lys Gly Ala Lys Cys Ser Arg Leu Met Tyr Asp Cys Cys
1               5                   10                  15

Thr Gly Ser Cys Arg Ser Gly Lys Cys
            20                  25

<210> SEQ ID NO 9
<211> LENGTH: 26
<212> TYPE: PRT
<213> ORGANISM: conus magus

<400> SEQUENCE: 9

Cys Lys Gly Lys Gly Ala Pro Cys Arg Lys Thr Met Tyr Asp Cys Cys
1               5                   10                  15

Ser Gly Ser Cys Gly Arg Arg Gly Lys Cys
            20                  25

<210> SEQ ID NO 10
<211> LENGTH: 27
<212> TYPE: PRT
<213> ORGANISM: conus geographus
<220> FEATURE:
<221> NAME/KEY: misc_feature
<223> OTHER INFORMATION: Pro at positions 4, 10 and 21 is 4-Hyp

<400> SEQUENCE: 10

Cys Lys Ser Pro Gly Ser Ser Cys Ser Pro Thr Ser Tyr Asn Cys Cys
1               5                   10                  15

Arg Ser Cys Asn Pro Tyr Thr Lys Arg Cys Tyr
            20                  25

<210> SEQ ID NO 11
```

```
<211> LENGTH: 18
<212> TYPE: DNA
<213> ORGANISM: conus catus

<400> SEQUENCE: 11
agcggcaccg taggtaga                                                 18

<210> SEQ ID NO 12
<211> LENGTH: 382
<212> TYPE: DNA
<213> ORGANISM: conus catus
<220> FEATURE:
<221> NAME/KEY: CDS
<222> LOCATION: (10)..(228)

<400> SEQUENCE: 12 atcatcaaa atg aaa ctg acg tgt gtg gtg atc gtc gcc gtg ctg ctc ctg   51
          Met Lys Leu Thr Cys Val Val Ile Val Ala Val Leu Leu Leu
          1               5                   10 acg gcc tgt caa ctc atc aca gct aat gac tcc aga ggt acg cag aag     99
Thr Ala Cys Gln Leu Ile Thr Ala Asn Asp Ser Arg Gly Thr Gln Lys
15                  20                  25                  30 cat cgt gcc ctg agg tcg gac acc aaa ctc tcc atg tcg act cgc tgc    147
His Arg Ala Leu Arg Ser Asp Thr Lys Leu Ser Met Ser Thr Arg Cys
                35                  40                  45 aag agt aaa gga gca aaa tgt tca aag ctt atg tat gac tgc tgc agc    195
Lys Ser Lys Gly Ala Lys Cys Ser Lys Leu Met Tyr Asp Cys Cys Ser
            50                  55                  60 ggt tct tgc agc ggc acc gta ggt aga tgt ggc tgatccggcg cttgatctcc  248
Gly Ser Cys Ser Gly Thr Val Gly Arg Cys Gly
65                  70 cccttctgtg ctctatcctt ttctgcctga gtcctcctta cctgagagtg gtcatgaacc  308
actcatcacc tacccctgg aggtctcaaa gaactacttg aaataaagcc gcttgcaaaa   368
aaaaaaaaaa aaaa                                                   382

<210> SEQ ID NO 13
<211> LENGTH: 73
<212> TYPE: PRT
<213> ORGANISM: conus catus

<400> SEQUENCE: 13

Met Lys Leu Thr Cys Val Val Ile Val Ala Val Leu Leu Leu Thr Ala
1               5                   10                  15

Cys Gln Leu Ile Thr Ala Asn Asp Ser Arg Gly Thr Gln Lys His Arg
            20                  25                  30

Ala Leu Arg Ser Asp Thr Lys Leu Ser Met Ser Thr Arg Cys Lys Ser
        35                  40                  45

Lys Gly Ala Lys Cys Ser Lys Leu Met Tyr Asp Cys Cys Ser Gly Ser
    50                  55                  60

Cys Ser Gly Thr Val Gly Arg Cys Gly
65                  70

<210> SEQ ID NO 14
<211> LENGTH: 27
<212> TYPE: PRT
<213> ORGANISM: conus catus

<400> SEQUENCE: 14

Cys Arg Ser Lys Gly Ala Lys Cys Ser Lys Leu Met Tyr Asp Cys Cys
1               5                   10                  15
```

Ser Gly Ser Cys Ser Gly Thr Val Gly Arg Cys
            20                  25

<210> SEQ ID NO 15
<211> LENGTH: 27
<212> TYPE: PRT
<213> ORGANISM: conus catus

<400> SEQUENCE: 15

Cys Lys Ser Lys Gly Ala Arg Cys Ser Lys Leu Met Tyr Asp Cys Cys
1               5                   10                  15

Ser Gly Ser Cys Ser Gly Thr Val Gly Arg Cys
            20                  25

<210> SEQ ID NO 16
<211> LENGTH: 27
<212> TYPE: PRT
<213> ORGANISM: conus catus

<400> SEQUENCE: 16

Cys Lys Ser Lys Gly Ala Gln Cys Ser Lys Leu Met Tyr Asp Cys Cys
1               5                   10                  15

Ser Gly Ser Cys Ser Gly Thr Val Gly Arg Cys
            20                  25

<210> SEQ ID NO 17
<211> LENGTH: 27
<212> TYPE: PRT
<213> ORGANISM: conus catus

<400> SEQUENCE: 17

Cys Lys Ser Lys Gly Ala Lys Cys Ser Lys Leu Met Tyr Asp Cys Cys
1               5                   10                  15

Ser Gly Ser Cys Ser Gly Ala Val Gly Arg Cys
            20                  25

<210> SEQ ID NO 18
<211> LENGTH: 27
<212> TYPE: PRT
<213> ORGANISM: Artificial Sequence
<220> FEATURE:
<223> OTHER INFORMATION: Description of Artificial Sequence: A
      derivative of CVID

<400> SEQUENCE: 18

Cys Lys Ser Lys Gly Ala Lys Cys Asp Lys Leu Met Tyr Asp Cys Cys
1               5                   10                  15

Ser Gly Ser Cys Ser Gly Thr Val Gly Arg Cys
            20                  25

<210> SEQ ID NO 19
<211> LENGTH: 27
<212> TYPE: PRT
<213> ORGANISM: Artificial Sequence
<220> FEATURE:
<223> OTHER INFORMATION: Description of Artificial Sequence: A
      derivative of CVID

<400> SEQUENCE: 19

Cys Lys Tyr Lys Gly Ala Lys Cys Ser Arg Leu Met Tyr Asp Cys Cys
1               5                   10                  15

Ser Gly Ser Cys Ser Gly Thr Val Gly Arg Cys
            20                  25

```
<210> SEQ ID NO 20
<211> LENGTH: 27
<212> TYPE: PRT
<213> ORGANISM: Artificial Sequence
<220> FEATURE:
<223> OTHER INFORMATION: Description of Artificial Sequence: A
      derivative of CVID

<400> SEQUENCE: 20

Cys Lys Ser Lys Gly Ala Lys Cys Ser Lys Leu Ala Tyr Asp Cys Cys
 1               5                  10                  15

Ser Gly Ser Cys Ser Gly Thr Val Gly Arg Cys
            20                  25

<210> SEQ ID NO 21
<211> LENGTH: 27
<212> TYPE: PRT
<213> ORGANISM: Artificial Sequence
<220> FEATURE:
<223> OTHER INFORMATION: Description of Artificial Sequence: A
      derivative of CVID

<400> SEQUENCE: 21

Cys Lys Ser Lys Gly Ala Lys Cys Ser Lys Leu Met Tyr Asp Cys Cys
 1               5                  10                  15

Thr Gly Ser Cys Ser Gly Thr Val Gly Arg Cys
            20                  25

<210> SEQ ID NO 22
<211> LENGTH: 27
<212> TYPE: PRT
<213> ORGANISM: Artificial Sequence
<220> FEATURE:
<223> OTHER INFORMATION: Description of Artificial Sequence: A
      derivative of CVID
<220> FEATURE:
<221> NAME/KEY: misc_feature
<222> LOCATION: (5)
<223> OTHER INFORMATION: Xaa at position 5 is D-alanine

<400> SEQUENCE: 22

Cys Lys Ser Lys Xaa Ala Lys Cys Ser Lys Leu Met Tyr Asp Cys Cys
 1               5                  10                  15

Ser Gly Ser Cys Ser Gly Thr Val Gly Arg Cys
            20                  25

<210> SEQ ID NO 23
<211> LENGTH: 28
<212> TYPE: PRT
<213> ORGANISM: Artificial Sequence
<220> FEATURE:
<223> OTHER INFORMATION: Description of Artificial Sequence: A
      derivative of CVID

<400> SEQUENCE: 23

Cys Lys Ser Lys Gly Ala Lys Cys Ser Lys Leu Met Tyr Asp Cys Cys
 1               5                  10                  15

Ser Gly Ser Cys Ser Gly Thr Val Gly Arg Cys Tyr
            20                  25

<210> SEQ ID NO 24
<211> LENGTH: 27
<212> TYPE: PRT
<213> ORGANISM: Artificial Sequence
<220> FEATURE:
<223> OTHER INFORMATION: Description of Artificial Sequence: A
```

-continued derivative of CVID

<400> SEQUENCE: 24

Cys Lys Ser Lys Gly Ala Lys Cys Ser Lys Leu Met Tyr Asp Cys Cys
1               5                   10                  15

Ser Gly Ser Cys Ser Gly Thr Val Gly Arg Cys
            20                  25

<210> SEQ ID NO 25
<211> LENGTH: 28
<212> TYPE: PRT
<213> ORGANISM: Artificial Sequence
<220> FEATURE:
<223> OTHER INFORMATION: Description of Artificial Sequence: A
      derivative of CVID

<400> SEQUENCE: 25

Tyr Cys Lys Ser Lys Gly Ala Lys Cys Ser Lys Leu Met Tyr Asp Cys
1               5                   10                  15

Cys Ser Gly Ser Cys Ser Gly Thr Val Gly Arg Cys
            20                  25

<210> SEQ ID NO 26
<211> LENGTH: 27
<212> TYPE: PRT
<213> ORGANISM: Artificial Sequence
<220> FEATURE:
<223> OTHER INFORMATION: Description of Artificial Sequence: A
      derivative of CVID
<220> FEATURE:
<221> NAME/KEY: misc_feature
<223> OTHER INFORMATION: Cysteine at position 1 is acylated

<400> SEQUENCE: 26

Cys Lys Ser Lys Gly Ala Lys Cys Ser Lys Leu Met Tyr Asp Cys Cys
1               5                   10                  15

Ser Gly Ser Cys Ser Gly Thr Val Gly Arg Cys
            20                  25

<210> SEQ ID NO 27
<211> LENGTH: 27
<212> TYPE: PRT
<213> ORGANISM: Artificial Sequence
<220> FEATURE:
<223> OTHER INFORMATION: Description of Artificial Sequence: A
      derivative of CVID
<220> FEATURE:
<221> NAME/KEY: misc_feature
<222> LOCATION: (12)
<223> OTHER INFORMATION: Leu at position 12 is L-norleucine

<400> SEQUENCE: 27

Cys Lys Ser Lys Gly Ala Lys Cys Ser Lys Leu Leu Tyr Asp Cys Cys
1               5                   10                  15

Ser Gly Ser Cys Ser Gly Thr Val Gly Arg Cys
            20                  25

<210> SEQ ID NO 28
<211> LENGTH: 27
<212> TYPE: PRT
<213> ORGANISM: Artificial Sequence
<220> FEATURE:
<223> OTHER INFORMATION: Description of Artificial Sequence: A
      derivative of CVID
<220> FEATURE:
<221> NAME/KEY: misc_feature
<222> LOCATION: (12)

```
<223> OTHER INFORMATION: Leu at position 12 is L-norleucine

<400> SEQUENCE: 28

Cys Lys Ser Lys Gly Ala Lys Cys Ser Arg Leu Leu Tyr Asp Cys Cys
1               5                   10                  15

Ser Gly Ser Cys Ser Gly Thr Val Gly Arg Cys
            20                  25

<210> SEQ ID NO 29
<211> LENGTH: 27
<212> TYPE: PRT
<213> ORGANISM: Artificial Sequence
<220> FEATURE:
<223> OTHER INFORMATION: Description of Artificial Sequence: A
      derivative of CVID
<220> FEATURE:
<221> NAME/KEY: misc_feature
<222> LOCATION: (12)
<223> OTHER INFORMATION: Leu at position 12 is L-norleucine

<400> SEQUENCE: 29

Cys Lys Tyr Lys Gly Ala Lys Cys Ser Arg Leu Leu Tyr Asp Cys Cys
1               5                   10                  15

Ser Gly Ser Cys Ser Gly Thr Val Gly Arg Cys
            20                  25

<210> SEQ ID NO 30
<211> LENGTH: 27
<212> TYPE: PRT
<213> ORGANISM: Artificial Sequence
<220> FEATURE:
<223> OTHER INFORMATION: Description of Artificial Sequence: A
      derivative of CVID
<220> FEATURE:
<221> NAME/KEY: misc_feature
<222> LOCATION: (12)
<223> OTHER INFORMATION: Xaa at position 12 is L-O-methyl homoserine

<400> SEQUENCE: 30

Cys Lys Ser Lys Gly Ala Lys Cys Ser Lys Leu Xaa Tyr Asp Cys Cys
1               5                   10                  15

Ser Gly Ser Cys Ser Gly Thr Val Gly Arg Cys
            20                  25

<210> SEQ ID NO 31
<211> LENGTH: 27
<212> TYPE: PRT
<213> ORGANISM: Artificial Sequence
<220> FEATURE:
<223> OTHER INFORMATION: Description of Artificial Sequence: A
      derivative of CVID
<220> FEATURE:
<221> NAME/KEY: misc_feature
<222> LOCATION: (12)
<223> OTHER INFORMATION: Methionine residue at position 12 is oxidised
      to its sulfoxide

<400> SEQUENCE: 31

Cys Lys Ser Lys Gly Ala Lys Cys Ser Lys Leu Xaa Tyr Asp Cys Cys
1               5                   10                  15

Ser Gly Ser Cys Ser Gly Thr Val Gly Arg Cys
            20                  25

<210> SEQ ID NO 32
<211> LENGTH: 27
<212> TYPE: PRT
<213> ORGANISM: Artificial Sequence
```

```
<220> FEATURE:
<223> OTHER INFORMATION: Description of Artificial Sequence: A
      derivative of CVID

<400> SEQUENCE: 32

Cys Lys Ser Lys Gly Ala Lys Cys Ser Lys Leu Met Tyr Asp Cys Cys
1               5                  10                  15

Ser Gly Ser Cys Ser Gly Thr Val Gly Arg Cys
            20                  25

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: A modified
      version of the second loop of CVID

<400> SEQUENCE: 33

Asp Lys Leu Met Tyr Asp
1               5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: A modified
      version of the second loop of CVID

<400> SEQUENCE: 34

Ser Lys Leu Ala Tyr Asp
1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: A modified
      version of the second loop of CVID
<220> FEATURE:
<221> NAME/KEY: misc_feature
<223> OTHER INFORMATION: Leu at position 4 is L-norleucine

<400> SEQUENCE: 35

Ser Lys Leu Leu Tyr Asp
1               5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: A modified
      version of the second loop of CVID
<220> FEATURE:
<221> NAME/KEY: misc_feature
<223> OTHER INFORMATION: Leu at position 4 is L-norleucine

<400> SEQUENCE: 36

Ser Arg Leu Leu Tyr Asp
1               5

<210> SEQ ID NO 37
<211> LENGTH: 6
<212> TYPE: PRT
<213> ORGANISM: Artificial Sequence
```

```
<220> FEATURE:
<223> OTHER INFORMATION: Description of Artificial Sequence: A modified
      version of the second loop of CVID
<220> FEATURE:
<221> NAME/KEY: misc_feature
<222> LOCATION: (4)
<223> OTHER INFORMATION: Xaa at position 4 is L-O-methyl homoserine

<400> SEQUENCE: 37

Ser Lys Leu Xaa Tyr Asp
1               5

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: A modified
      version of the second loop of CVID
<220> FEATURE:
<221> NAME/KEY: misc_feature
<222> LOCATION: (4)
<223> OTHER INFORMATION: Xaa at position 4 is L-O-methyl serine

<400> SEQUENCE: 38

Ser Lys Leu Xaa Tyr Asp
1               5

<210> SEQ ID NO 39
<211> LENGTH: 26
<212> TYPE: PRT
<213> ORGANISM: Artificial Sequence
<220> FEATURE:
<223> OTHER INFORMATION: Description of Artificial Sequence: primer
<220> FEATURE:
<221> NAME/KEY: misc_feature
<222> LOCATION: (2)..(4)
<223> OTHER INFORMATION: Xaa may be any other amino acid and up to one
      Xaa may be a deletion
<220> FEATURE:
<221> NAME/KEY: misc_feature
<222> LOCATION: (6)..(7)
<223> OTHER INFORMATION: Xaa may be any other amino acid and up to one
      Xaa may be a deletion
<220> FEATURE:
<221> NAME/KEY: misc_feature
<222> LOCATION: (9)
<223> OTHER INFORMATION: Xaa may be any other amino acid and up to one
      Xaa may be a deletion
<220> FEATURE:
<221> NAME/KEY: misc_feature
<222> LOCATION: (12)
<223> OTHER INFORMATION: Xaa may be any other amino acid and up to one
      Xaa may be a deletion
<220> FEATURE:
<221> NAME/KEY: misc_feature
<222> LOCATION: (14)
<223> OTHER INFORMATION: Xaa may be any other amino acid and up to one
      Xaa may be a deletion
<220> FEATURE:
<221> NAME/KEY: misc_feature
<222> LOCATION: (17)
<223> OTHER INFORMATION: Xaa may be any other amino acid and up to one
      Xaa may be a deletion
<220> FEATURE:
<221> NAME/KEY: misc_feature
<222> LOCATION: (22)
<223> OTHER INFORMATION: Xaa may be any other amino acid and up to one
      Xaa may be a deletion

<400> SEQUENCE: 39

Cys Xaa Xaa Xaa Gly Xaa Xaa Cys Xaa Lys Leu Xaa Tyr Xaa Cys Cys
1               5                   10                  15
```

-continued

```
Xaa Ser Cys Ser Gly Xaa Val Gly Arg Cys
        20                  25

<210> SEQ ID NO 40
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 40
aactggaaga attcgcggcc gcaggaat                                        28

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 41
atcatcaaaa tgaaactgac gtc                                             23

<210> SEQ ID NO 42
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 42
aactggaaga attcgcggcc gcaggaat                                        28

<210> SEQ ID NO 43
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 43
atcaaaatga aactgacgtg tgtggtg                                         27

<210> SEQ ID NO 44
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 44
gcgttttgat cagccacatc taccta                                          26
```